US00PP21137P3

(12) United States Plant Patent
Maillard et al.

(10) Patent No.: US PP21,137 P3
(45) Date of Patent: Jul. 6, 2010

(54) APRICOT TREE NAMED 'ASFCOT0405'
(50) Latin Name: *Prunus armeniaca*
Varietal Denomination: ASFCOT0405

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/382,110

(22) Filed: Mar. 9, 2009

(65) Prior Publication Data

US 2009/0235400 P1 Sep. 17, 2009

(30) Foreign Application Priority Data

Mar. 17, 2008 (QZ) ..... PBR 2008/0593

(51) Int. Cl.
*A01H 5/00* (2006.01)

(52) U.S. Cl. ..... Plt./186

(58) Field of Classification Search ..... Plt./186
See application file for complete search history.

*Primary Examiner*—Annette H Para
(74) *Attorney, Agent, or Firm*—Westerman, Hattori, Daniels & Adrian, LLP

(57) ABSTRACT

A new and distinct variety of apricot tree, denominated 'ASFCOT0405', has fruits of very long shelf life without alteration after harvesting, of mildly acidic and sweet taste, with an attractive bright orange fruit skin covered by an appealing red blush.

4 Drawing Sheets

Latin name of the genus and species claimed: *Prunus armeniaca.*

Varietal denomination: 'ASFCOT0405'.

BACKGROUND OF THE NEW VARIETY

The present invention relates to a new and distinct variety of apricot tree, *Prunus armeniaca,* which has been given the variety denomination 'ASFCOT0405'. This new variety results from our plant-breeding program aimed at obtaining apricot trees producing fruits of sweet and aromatic taste, with an attractive bright orange fruit skin covered by an appealing red blush. One of our main concerns is also the production of new varieties producing fruits with a long shelf life after harvesting, in order to facilitate long-distance shipping. Our final purpose is the production of a range of new apricot tree varieties differing by their time of maturity, while producing fruits of very similar characteristics, in order to provide markets with almost indistinguishable fruits during the whole period of production of apricots.

The present new variety ripens at the end of June in the Pyrénées-Orientales departement, France. Contrast is made to 'Couloumine' (Orange Ruby®) (non-patented), a standard apricot variety, and to 'Robada' (U.S. Plant Pat. No. 9,890) and 'Toyaco' (Tom Cot®) (patent status unknown) apricot trees, parents of the new variety, for reliable description. 'ASFCOT0405' is a promising candidate for commercial success in that it has very attractive fruits of long shelf life after harvesting.

ORIGIN OF THE VARIETY

The 'ASFCOT0405' apricot tree originated in a cultivated area of the south of France, in the Pyrénées-Orientales departement, where it was tested. The 'ASFCOT0405' variety was produced by controlled pollination. The seed parent was the 'Robada' (U.S. Plant Pat. No. 9,890) apricot tree and the pollen parent was the 'Toyaco' (Tom Cot®) (patent status unknown) apricot tree. 'ASFCOT0405' was provisionally designated, tested and genetically identified by a genetic profile, under number 03.16.01 AB and was registered at the Official Catalogue of the Agriculture Ministry of the French Republic on Nov. 14, 2007 under number 1024474 and name 'ABCOT0405'. It was obtained by hybridizing and propagated by grafting on a Franc INRA Montclar® (non-patented) rootstock tree. It has been determined to have unique tree and fruit characteristics making it worthy for commercial fresh fruit production. There are no known effects of the standard Franc INRA Montclar® (non-patented) rootstock on the scion cultivar. Asexually propagated plants remained true to the original tree and all characteristics of the tree and the fruit were transmitted. The plant was reproduced asexually by us in Elne, Pyrénées-Orientales departement, France.

SUMMARY OF THE VARIETY

The new and distinct variety of apricot tree blooms in March at Perpignan in the Pyrénées-Orientales departement, France. More particularly, it approximately blooms between the $9^{th}$ and the $20^{th}$ of March, generally 2 to 3 days earlier than 'Couloumine' (Orange Ruby®) (non-patented).

The first fruit of 'ASFCOT0405' apricot tree ripens at the end of June, approximately 2 days later than the first fruit of the 'Couloumine' (Orange Ruby®) (non-patented) variety. More particularly, it approximately ripens between June $22^{th}$ and June $30^{th}$. The date of maturity varies slightly with the prevailing climatic conditions.

DESCRIPTION OF THE DRAWINGS

In the accompanying drawing, which are as nearly true as it is reasonably possible to make in a color illustration of this type.

Figure 1:
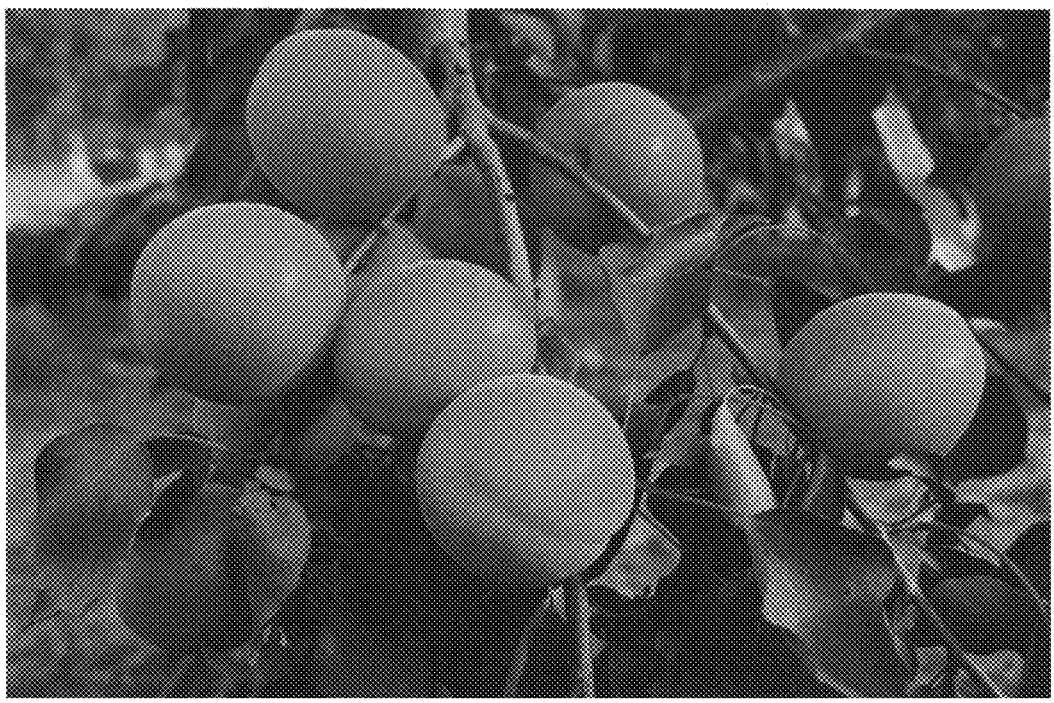
FIG. 1 is a color photograph, which shows a twig bearing typical fruit specimens of the new variety, and leaves of the new variety.
Figure 2:
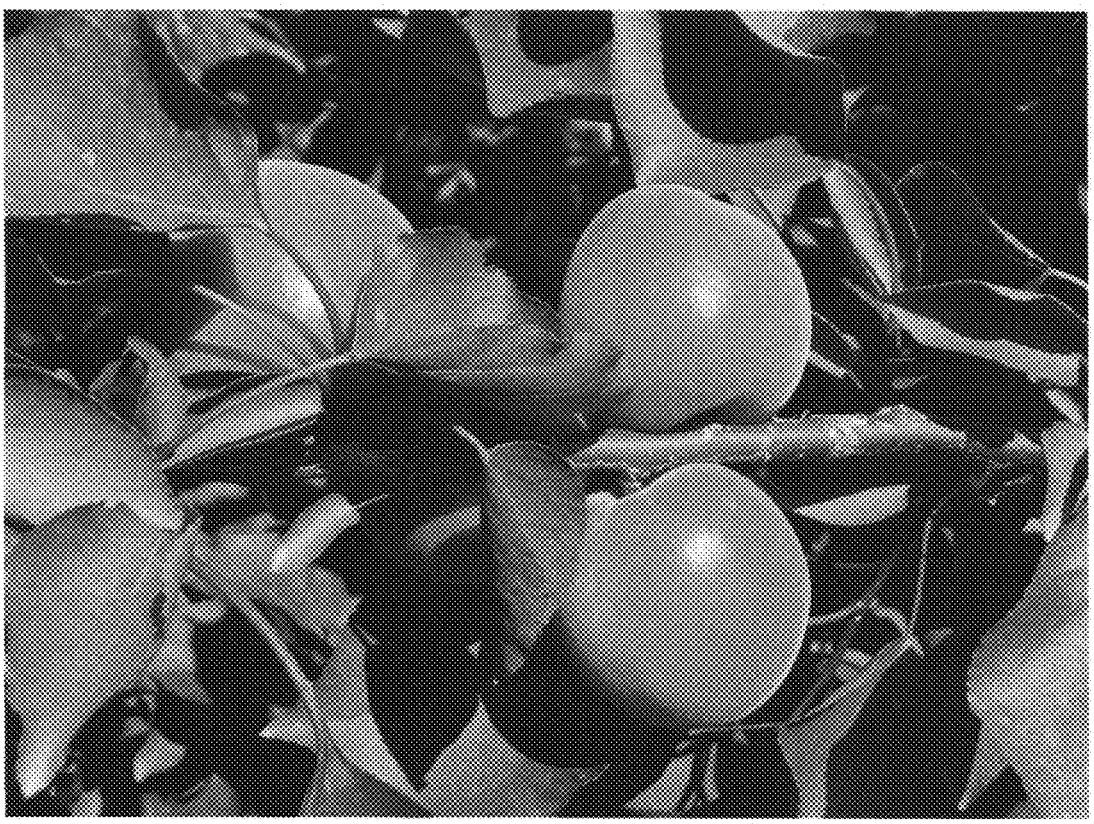
FIG. 2 is a color photograph, which shows a twig bearing three typical fruit specimens of the new variety, and leaves of the new variety.
Figure 3:
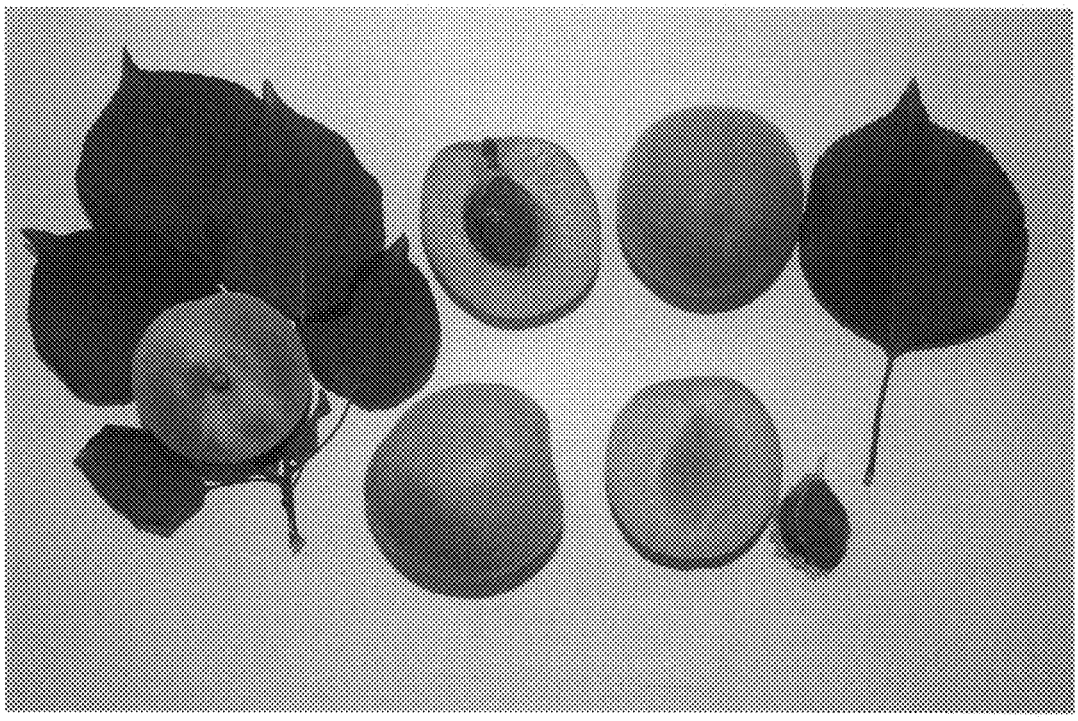
FIG. 3 is a color photograph, which shows three whole fruits of the new variety and a fourth fruit cut in half with the stone left in one of the halves for depicting the fruit flesh, the pit cavity and the stone of the new variety.
Figure 4:
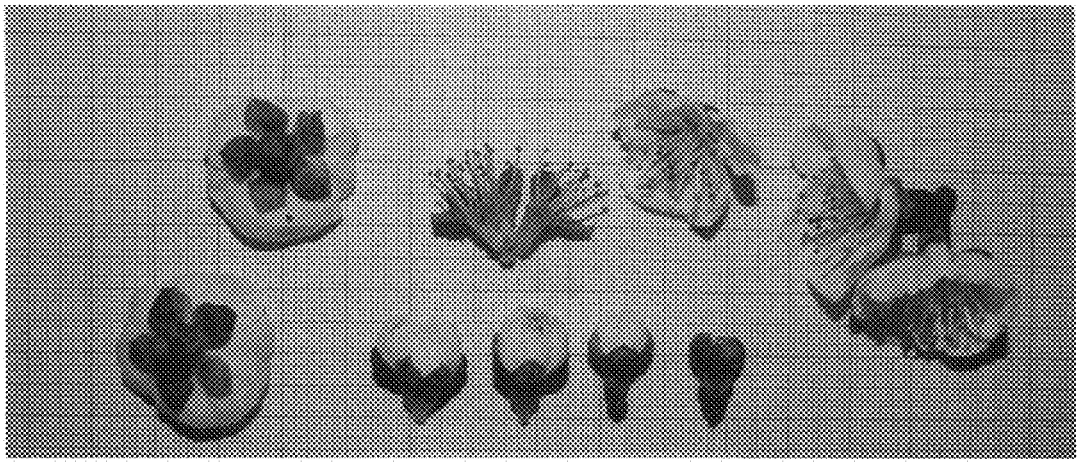
FIG. 4 is a color photograph with reverse and size views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'ASFCOT0405' is high, due to fruit very long shelf life without alteration after harvesting.

Trees are vigorous and of large stature half-standing in a semi-upright out aspect. The anthocyanic coloration of flowering shoot is present excluding brushwood side away from sun. Flowering begins semi-early in springtime. Time of maturity for consumption is semi-early to semi-late. The fruit color is an orange red blush on 40 to 60% of the fruit skin surface, on an yellow orange background. Fruit taste is mildly acidic and sweet, aromatic.

'ASFCOT0405' variety blooms generally 2 to 3 days earlier and ripens 2 days later than 'Couloumine' (Orange Ruby®) (non-patented). 'ASFCOT0405' fruits are considered superior to 'Couloumine' fruits because of the following characteristics: they are bigger, rounder, more homogeneous between them, of better eating quality, more juicy, while firmer and holding their firmness over the time. 'ASFCOT0405' trees also produce fruits more quickly than 'Couloumine' trees.

The new variety male parent, which is 'Toyaco' (Tom Cot®) (patent status unknown), differs from the new variety because of the following characteristics: 'Toyaco' trees are less vigourous, bloom earlier, are self-fruifful instead of partially self-fruifful, produce more flowers and imperatively requires thinning.

The new variety female parent, which is 'Robada' (U.S. Plant Pat. No. 9,890), differs from the new variety because of the following characteristics: 'Robada' trees are less vigourous, have semi-upright shape, bloom later and are not self-fruitful.

DETAILED DESCRIPTION

Referring more specifically to the pomological details of this new and distinct variety of apricot tree, the following was observed during the 2007 and 2008 growing seasons under the ecological conditions prevailing at the orchards located near the town of Elne, Pyrénées-Orientales departement, France. All observations have been done on rootstock cultivar. The rootstock was a Franc INRA Montclar® (non-patented) tree. More particularly, observations relative to tree, trunk, branches, were done during Summer 2008 on trees in their third growing season; observations relative to leaves and fruit were done during Summer 2008 on trees in their fourth growing season; observations relative to flowers were done in March 2007 on trees in their fourth growing season. All major color code designations are by reference to The R.H.S. Colour Chart (Fourth Edition) provided by The Royal Horticultural Society of Great Britain.

TREE

Size:

*Generally.*—Considered large as compared to other common commercial apricot cultivars. Trees reached about 250 cm during the first growing season. New shoots grew of about 100 cm every following year. Trees were pruned every year after the second growing season to a height of approximately 250 cm.

Spread: Approximately 200 cm. The whole orchard was oriented to a central leader organisation, with tree lines spaced of 4.0 meters and trees spaced of 1 meter in a same tree line.

Vigor: Considered vigorous. The present variety reached approximately 250 cm in height during the first growing season. For second and following seasons, the variety was pruned to an approximate height of 250 cm. Theses characteristics are dependant on prevailing climatic conditions, cultural practices and soils fertility.

Productivity: Very productive. Fruit set is spaced by thinning. However, the new variety only requires a medium thinning to obtain marketable size fruits.

Bearer: Regular. No alternate bearing observed.

Form: The 'ASFCOT0405' variety has naturally a semi-spread to semi-upright shape.

Density: Highly dense, in order to obtain fruits more quickly.

Fertility: Partially self-fertile. Tests were done under sterile bags and confirmed in orchard.

Chilling requirement: The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. The tree also seems to have a good resistance to frosty springtime weather.

TRUNK

Diameter: Approximately about 8.0 cm in diameter when measured at a distance of approximately 30 cm above the soil level.

Bark texture: Considered smooth to rough when numerous lenticels are present.

Bark coloration: The bark has orange-brown (RHS Greyed Orange 166 A) and green-grey (RHS Greyed Green 197 A) colorations.

Lenticels:

*Color.*—A light grey (RHS Greyed White group 156 A).

*Density.*—About 5 lenticels per square cm.

*Size.*—Lenticels are approximately 1.0 millimeters wide, and 4.0 millimeters long.

BRANCHES

Size: Current season shoots are considered medium for the variety and mature branches are considered medium to thick.

Diameter: Average as compared to other apricot varieties. The current season shoots have a diameter of about 6.0 millimeters, and branches of observed trees have a diameter comprised between 25.0 and 30.0 millimeters.

Surface texture: New growth smooth. Mature growth medium rough, roughness increases with age.

Crotch angles: The crotch angles are generally between 50 degrees and 70 degrees from the horizontal axis.

Internode length: Generally between 15.0 and 20.0 millimeters.

Color of mature branches: Orange brown to green brown (RHS Greyed Orange 166 A to Greyed Green 197 B).

Color of current seasons shoots: Orange brown (RHS Greyed Orange 165 A to B) on exposed areas to grey-brown (RHS Grey Brown 199 A) on non-exposed areas, turning to mature branches color when aging.
Vigor: Vigorous.
Lenticels:
*Color.*—A light grey (RHS Greyed White group 156 A).
*Density.*—About 5 lenticels per square cm, particularly on mature branches.
*Size.*—Slightly smaller than trunk's lenticels, they are approximately 0.8 millimeters wide, and 3.0 millimeters long.

LEAVES
Size: Considered medium for the species.
Length: Approximately 92.0 to 117.0 millimeters without leaf petiole.
Width: Approximately 94.0 to 100.0 millimeters.
Form: Almost circular.
Apex: Acuminate.
Base: Rounded.
Margins: Dentate.
Thickness: Medium.
Upper surface texture: Smooth.
Lower surface texture: Smooth.
Leaf color:
*Upper leaf surface.*—Green (RHS Green 136 A).
*Lower surface.*—Green (RHS Green 139 B).
Leaf venation: Pinnately veined.
Mid-vein thickness: Approximately 1.5 millimeters when measured at the base of the leaf.
Mid-vein color: Red Purple (RHS Red Purple Group 59 B).
Other veins color: Green (RHS Green Group 143 B).
Uniformity: Leaves are of medium size. No stipules are generally found.
Petiole:
*Size.*—Generally large.
*Length.*—Between 40.0 and 50.0 millimeters.
*Diameter.*—Approximately 1.5 millimeters.
*Surface.*—Smooth.
*Color.*—Depending on climatic conditions, the antocyanic coloration on petiole's upper face can be very present and varies from red (RHS Red Group 53 B) to red purple (RHS Red Purple Group 59 B).
Leaf glands:
*Size.*—Considered small.
*Length.*—About 0.7 millimeters.
*Width.*—About 0.7 millimeters.
*Number.*—Generally 1 to 4 glands per leaf, usually 2.
*Type.*—Round.
*Position.*—Alternatively located on upper portion of petiole, also located on lower portion of leaf blade.
*Color.*—Generally greyed orange (RHS Greyed Orange 165 A).
Leaf stipules:
*Generally.*—No leaf stipules observed.

FLOWERS
Flower buds:
*Generally.*—At pre-floral stage of development, the floral buds are conic in form with a very rounded tip. Their form is evolving until blooming, with variables dimensions. Just before blooming, floral buds are approximately between 12.0 and 14.0 millimeters wide and approximately 16.0 millimeters long. Flower buds are generally alone or in groups of 2 or 3.
*Color.*—This characteristic is dependent upon the proximity to bloom. At pre-floral stage of development, the bottom of the flowers buds, formed by the sepals, is of purple-brown color (RHS Greyed Purple 183 B to C); the corolla, formed by the petals, is generally of white color with slight pink touches (RHS White N 155 B to C).
Texture: Smooth.
Hardiness: No winter injury was noted during the last several years of evaluation in the central Pyrénées-Orientales departement, with winter temperatures as low as −10 degrees Celsius in January.
Pedicel:
*Length.*—About 3.0 millimeters.
*Width.*—About 2.0 millimeters.
Date of bloom: Generally March.
First bloom: Mar. 9, 2006.
Full bloom: Mar.13, 2006.
Petal fall: Mar. 20, 2006.
Blooming time: Considered semi-early season in relative comparison to other commercial apricot cultivars.
Duration of bloom: Approximately 13 days.
Flower size: Flower diameter at full bloom is approximately 21.0 to 25.0 millimeters.
Bloom quantity: Considered very abundant, flowers are generally found in bunches.
Flower bud frequency: Generally 1 flower bud or several flower buds per groups of 2 to 3 appear per node.
Petal size:
*Generally.*—Considered small for the species.
*Length.*—Generally about 15.0 millimeters.
*Width.*—Generally about 15.0 millimeters.
Petal form: Round.
Petal count: Generally 5, overlapping sepals.
Petal texture: Smooth.
Petal color: Petal color evolves from a very light pink at popping stage, to white (RHS White Group N 155 B to C).
Fragrance: Slight.
Petal base: Narrow at point of attachment.
Petal apex: Round.
Petal peduncle:
*Length.*—Approximately 4.0 to 5.0 millimeters.
*Diameter.*—Approximately 1.5 millimeters.
*Color.*—Generally yellow-green (RHS Yellow Green 145 C), with highlights of red (RHS Red 46 D).
Sepals:
*Size.*—Generally small.
*Sepal count.*—5.
*Form.*—Triangular, apex slightly pointed.
*Color.*—Purple-brown (RHS Greyed Purple 183 B to C).
*Texture.*—Glabrous.
Stamens:
*Average number of stamens per flower.*—Approximately 30 stamens per flower.
*Length.*—Average.
Filaments:
*Size.*—Approximately 6.0 to 12.0 millimeters in length.
*Color.*—Considered white (RHS White Group N 155 B).
Anthers:
*Color.*—Orange yellow (RHS Yellow Orange 16 D).
Pistil:
*Number.*—Usually 1.
*Length.*—Approximately 10.0 to 16.0 millimeters including the ovary; Generally at the same level than anthers.
*Color.*—Considered a very pale green (varying from RHS Yellow Green 150 D to RHS Yellow Green 151 D).
*Pubescence.*—Present.
Pollen:
*Pollen production.*—Pollen is abundant, and partially self-fruitful.

*Color.*—Orange yellow color (RHS Yellow Orange 16 D).

Calyx:

*Internal surface texture.*—Glabrous.

*Color.*—The outer surface of the calyx is considered of Purple (RHS Greyed Purple 183 B) color becoming lighter toward the base, the inner surface of the calyx is orange (RHS Yellow Orange group 22 A).

FRUIT

Maturity when described: Firm ripe condition (shipping ripe).

Date of first picking: Jun. 22, 2006.

Date of last picking: Jun. 30, 2006. The date of harvest varies slightly with the prevailing climatic conditions. The 'ASFCOT0405' variety has an semi-early to semi-late date of picking.

Size:

*Generally.*—Considered large.

*Length.*—Approximately 55.0 to 60.0 millimeters.

*Width.*—Approximately 55.0 millimeters.

*Thickness.*—Approximately 45.0 millimeters.

*Typical weight.*—Generally around 80.0 grams.

Fruit form:

*Generally.*—Round, slightly oblate toward both fruit apex and fruit base. The fruit is considered to be symmetrical.

Suture:

*Generally.*—Slightly marked, extending from the base to the apex. No apparent callousing or stitching exists along the suture line.

*Color.*—The suture has generally a color similar to the whole fruit color, an orange red blush (RHS Orange Red Group 34 A to RHS Orange Red Group N 34 A) on an yellow orange (RHS Yellow Orange Group 17 A) background.

*Ventral surface form.*—Rounded.

Apex: Straight to slightly oblique.

Base: Straight to slightly oblique.

Stem cavity: Shallow. Average depth of the stem cavity is about 0.5 cm. Average width is about 1.0 cm.

Stem:

*Size.*—Generally small. Stem length is about 4.0 millimeters and stem diameter about 2.5 millimeters.

*Color.*—Stem color is green varying from RHS Yellow green 145 B to RHS Green Group 143 C.

Fruit skin:

*Thickness.*—Considered average.

*Texture.*—Smooth.

*Pubescence.*—Present but very fine.

*Tendency to crack.*—None observed.

Color:

*Blush color.*—The blush color is an orange red (RHS Orange Red Group 34 A to RHS Orange Red Group N 34 A). The red blush covers 40% to 60% of the fruit skin surface. The darker blush color within the described range appears on fruits exposed to sunlight.

*Ground color.*—The ground color is considered a yellow orange (RHS Yellow Orange Group 17 A).

*Adherence to flesh.*—Very adherent.

*Taste.*—Mildly acid. Sweet.

Flesh:

*Ripens.*—Evenly.

*Texture.*—Fine and firm. Very melting at end of maturity.

*Fibers.*—Generally none observed.

*Aroma.*—Pronounced.

*Firmness.*—Firm. Holds firmness over the time.

*Eating quality.*—Considered very good, sweet.

*Flavor.*—Considered very good. Good balance between sweetness and acidity, very aromatic.

*Juice.*—Good juiciness, increasing with maturity.

*Brix.*—Usually between 13.0 and 15.0 degrees but can be higher. This characteristic varies slightly with the number of fruits per tree; prevailing cultural practices; and the surrounding climatic conditions.

*Flesh color.*—Orange (RHS Yellow Orange Group 21 C).

STONE

Stone cavity:

*Color.*—Orange (RHS Orange Group 26 A to B).

*Length.*—Between 25.0 and 30.0 millimeters.

Type: Free, although can be attached to the flesh through stone's base.

Size: Considered medium for the variety.

*Length.*—Approximately between 25.0 and 30.0 millimeters.

*Width.*—Approximately between 18.0 and 25.0 millimeters.

*Thickness.*—Approximately between 12.0 and 15.0 millimeters.

Stone form (viewed from stem end): Oval, flattened.

Stone base shape: Rounded to slightly concave.

Stone apex shape: Round, generally no point observed.

Stone surface:

*Surface texture.*—Medium to smooth.

Stone color: The color of the dry stone is generally considered a greyed orange (RHS Greyed Orange 164 A to B).

Kernel:

*Taste.*—Bitter.

Fruit use: The subject variety 'ASFCOT0405' produces fruits useful for all type of consumption, uncooked or cooked. They are also useful for both local markets and long distance shipping.

Keeping quality: Good. Fruits stored well during 3 weeks after harvest in a cold atmosphere. They stayed firm and kept their eating quality. Fruits are considered to have a long shelf life after harvesting, without alteration.

Shipping quality: The fruit of the new apricot variety showed very little skin scarring or flesh bruising in picking, packing and shipping trials.

Resistance to insects and disease: No susceptibilities were noted. Under close observation during planting, growing and harvesting of fruit, no particular plant/fruit disease resistance or susceptibility has been observed. Any variety observed during indexing of plant characteristics with abnormal fungus, bacterial, virus or insect susceptibility is destroyed and eliminated from our breeding program.

Although the new variety of apricot tree possesses the described characteristics noted above when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of apricot tree as illustrated and described, characterized by fruits of very long shelf life without alteration after harvesting, of mildly acidic and sweet taste, with an attractive bright orange fruit skin covered by an appealing red blush.

* * * * *